US008574424B2

(12) United States Patent
Deng

(10) Patent No.: US 8,574,424 B2
(45) Date of Patent: *Nov. 5, 2013

(54) SYSTEM AND METHODS FOR DETERMINATION OF ANALYTE CONCENTRATION USING TIME RESOLVED AMPEROMETRY

(75) Inventor: David Deng, Weston, FL (US)

(73) Assignee: Nipro Diagnostics, Inc., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/331,346

(22) Filed: Dec. 20, 2011

(65) Prior Publication Data
US 2012/0234700 A1 Sep. 20, 2012

Related U.S. Application Data

(63) Continuation of application No. 12/410,048, filed on Mar. 24, 2009, now Pat. No. 8,101,062, which is a continuation-in-part of application No. 12/179,853, filed on Jul. 25, 2008, now Pat. No. 8,088,272.

(60) Provisional application No. 60/952,076, filed on Jul. 26, 2007.

(51) Int. Cl.
*G01N 27/26* (2006.01)
*G01N 27/27* (2006.01)

(52) U.S. Cl.
USPC ............. 205/777.5; 205/778; 205/778.5; 205/779; 205/792; 205/793.5; 702/25; 702/100

(58) Field of Classification Search
USPC ............. 204/403.01, 403.02, 403.03, 403.04, 204/403.13, 403.14; 205/777.5, 778, 778.5, 205/779, 792, 793.5; 435/7.4, 10, 11, 12, 435/287.1, 287.2, 287.3, 817; 702/25, 100; 422/82.01, 82.02, 82.03, 98; 436/150, 436/151
See application file for complete search history.

(56) References Cited

U.S. PATENT DOCUMENTS

| | | | |
|---|---|---|---|
| 5,047,351 A | | 9/1991 | Makiuchi et al. |
| 5,942,102 A | | 8/1999 | Hodges et al. |
| 5,997,817 A | | 12/1999 | Crismore et al. |
| 6,153,069 A | * | 11/2000 | Pottgen et al. ........... 204/403.11 |
| 6,251,260 B1 | | 6/2001 | Heller et al. |
| 7,501,052 B2 | * | 3/2009 | Iyengar et al. ................ 205/775 |
| 8,088,272 B2 | * | 1/2012 | Deng ........................... 205/792 |
| 8,101,062 B2 | * | 1/2012 | Deng ........................ 205/777.5 |
| 8,123,920 B2 | * | 2/2012 | Iyengar et al. ........... 204/403.14 |
| 2003/0096420 A1 | * | 5/2003 | Heller .............................. 436/63 |
| 2003/0146110 A1 | | 8/2003 | Karinka et al. |
| 2004/0045821 A1 | | 3/2004 | Cui et al. |
| 2005/0049473 A1 | | 3/2005 | Desai et al. |
| 2006/0063218 A1 | | 3/2006 | Bartkowiak et al. |
| 2006/0074564 A1 | | 4/2006 | Bartkowiak et al. |
| 2006/0085137 A1 | | 4/2006 | Bartkowiak et al. |
| 2006/0191787 A1 | | 8/2006 | Wang et al. |
| 2007/0040567 A1 | | 2/2007 | Popovich et al. |
| 2007/0074977 A1 | | 4/2007 | Guo et al. |
| 2008/0020452 A1 | | 1/2008 | Popovich et al. |
| 2008/0102441 A1 | | 5/2008 | Chen et al. |
| 2008/0149480 A1 | | 6/2008 | Bell |
| 2009/0026094 A1 | | 1/2009 | Deng et al. |
| 2009/0076738 A1 | * | 3/2009 | Kayihan et al. ................. 702/25 |
| 2009/0152127 A1 | | 6/2009 | Kaimori et al. |
| 2009/0166225 A1 | * | 7/2009 | Iyengar et al. ................ 205/792 |
| 2012/0205259 A1 | * | 8/2012 | Iyengar et al. ................ 205/782 |

FOREIGN PATENT DOCUMENTS

| | | |
|---|---|---|
| EP | 1 256 798 A1 | 11/2002 |
| EP | 1 522 592 A1 | 4/2005 |
| EP | 1 557 663 A1 | 7/2005 |
| EP | 1 582 864 A1 | 10/2005 |
| EP | 1 770 396 A2 | 4/2007 |
| JP | 63-61147 A | 3/1988 |
| JP | 9-292387 A | 11/1997 |
| JP | 2001-526388 A | 12/2001 |
| JP | 2005-509161 A | 4/2005 |
| JP | 2005-512027 A | 4/2005 |
| WO | WO 03/040728 A2 | 5/2003 |
| WO | WO 03/044511 A2 | 5/2003 |
| WO | WO 2004/040289 A1 | 5/2004 |
| WO | WO 2007/032286 A1 | 3/2007 |
| WO | WO 2008/054608 A1 | 5/2008 |
| WO | WO 2009/015316 A1 | 1/2009 |

OTHER PUBLICATIONS

International Search Report and the Written Opinion of the International Searching Authority, PCT/US2008/071128, dated Nov. 21, 2008.
International Search Report and the Written Opinion of the International Searching Authority, PCT/US2008/071132, dated Nov. 26, 2008.
International Search Report and the Written Opinion of the International Searching Authority, PCT/US2010/023199, dated Jun. 2, 2010.
Pine Instrument Co., "Educator's Reference Guide for Electrochemistry" Manual: LMPROF1, Revision 003, Feb. 1, 2000; pp. 1-66.

* cited by examiner

*Primary Examiner* — Bruce Bell
(74) *Attorney, Agent, or Firm* — Finnegan, Henderson, Farabow, Garrett & Dunner LLP

(57) ABSTRACT

A method for determining a concentration of an analyte is disclosed. The method includes applying a potential excitation to a fluid sample containing an analyte and determining if a current decay curve associated with the fluid sample has entered an analyte depletion stage. The method also includes measuring a plurality of current values associated with the fluid sample during the analyte depletion stage and calculating an analyte concentration based on at least one of the plurality of current values.

23 Claims, 7 Drawing Sheets

SYSTEM AND METHODS FOR DETERMINATION OF ANALYTE CONCENTRATION USING TIME RESOLVED AMPEROMETRY

DESCRIPTION OF THE INVENTION

This application is a continuation of U.S. application Ser. No. 12/410,048, filed Mar. 24, 2009,now U.S. Pat. No. 8,101, 062 which is a continuation-in-part of U.S. application Ser. No. 12/179,853, filed Jul. 25, 2008, now U.S. Pat. No. 8,088, 272 which claims priority to U.S. Provisional Patent Application No. 60/952,076, filed Jul. 26, 2007, all of which are incorporated herein by reference in their entirety.

FIELD OF THE INVENTION

The present invention relates to the field of diagnostic testing systems for determining the concentration of an analyte in a solution and, more particularly, to systems and methods for measuring an analyte concentration using time resolved amperometry.

BACKGROUND OF THE INVENTION

The present disclosure relates to a biosensor system for measuring an analyte in a bodily fluid, such as blood. The system includes a process and system for improved determination of analyte concentration over a wide range of analyte concentrations.

Electrochemical sensors have long been used to detect or measure the presence of substances in fluid samples. Electrochemical sensors include a reagent mixture containing at least an electron transfer agent (also referred to as an "electron mediator") and an analyte specific bio-catalytic protein (e.g. a particular enzyme), and one or more electrodes. Such sensors rely on electron transfer between the electron mediator and the electrode surfaces and function by measuring electrochemical redox reactions. When used in an electrochemical biosensor system or device, the electron transfer reactions are monitored via an electrical signal that correlates to the concentration of the analyte being measured in the fluid sample.

The use of such electrochemical sensors to detect analytes in bodily fluids, such as blood or blood derived products, tears, urine, and saliva, has become important, and in some cases, vital to maintain the health of certain individuals. In the health care field, people such as diabetics, for example, must monitor a particular constituent within their bodily fluids. A number of systems are capable of testing a body fluid, such as, blood, urine, or saliva, to conveniently monitor the level of a particular fluid constituent, such as, cholesterol, proteins, and glucose. Patients suffering from diabetes, a disorder of the pancreas where insufficient insulin production prevents the proper digestion of sugar, have a need to carefully monitor their blood glucose levels on a daily basis. Routine testing and controlling blood glucose for people with diabetes can reduce their risk of serious damage to the eyes, nerves, and kidneys.

A number of systems permit people to conveniently monitor their blood glucose levels. Such systems typically include a test strip where the user applies a blood sample and a meter that "reads" the test strip to determine the glucose level in the blood sample. An exemplary electrochemical biosensor is described in U.S. Pat. No. 6,743,635 ('635 patent) which describes an electrochemical biosensor used to measure glucose level in a blood sample. The electrochemical biosensor system is comprised of a test strip and a meter. The test strip includes a sample chamber, a working electrode, a counter electrode, and fill-detect electrodes. A reagent layer is disposed in the sample chamber. The reagent layer contains an enzyme specific for glucose, such as, glucose oxidase, glucose dehydrogenase, and a mediator, such as, potassium ferricyanide or ruthenium hexamine. When a user applies a blood sample to the sample chamber on the test strip, the reagents react with the glucose in the blood sample and the meter applies a voltage to the electrodes to cause redox reactions. The meter measures the resulting current that flows between the working and counter electrodes and calculates the glucose level based on the current measurements.

In some instances, electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the particular blood hematocrit level (i.e. the percentage of the amount of blood that is occupied by red blood cells) can erroneously affect a resulting analyte concentration measurement. Another example can include various constituents affecting blood viscosity, cell lysis, concentration of charged species, pH, or other factors that may affect determination of an analyte concentration. For example, under certain conditions temperature could affect analyte readings and calculations.

Variations in a volume of red blood cells within blood can cause variations in glucose readings measured with disposable electrochemical test strips. Typically, a negative bias (i.e., lower calculated analyte concentration) is observed at high hematocrits, while a positive bias (i.e., higher calculated analyte concentration) is observed at low hematocrits. At high hematocrits, for example, the red blood cells may impede the reaction of enzymes and electrochemical mediators, reduce the rate of chemistry dissolution since there less plasma volume to solvate the chemical reactants, and slow diffusion of the mediator. These factors can result in a lower than expected glucose reading as less current is produced during the electrochemical process. Conversely, at low hematocrits, less red blood cells may affect the electrochemical reaction than expected, and a higher measured current can result. In addition, the blood sample resistance is also hematocrit dependent, which can affect voltage and/or current measurements.

Several strategies have been used to reduce or avoid hematocrit based variations on blood glucose. For example, test strips have been designed to incorporate meshes to remove red blood cells from the samples, or have included various compounds or formulations designed to increase the viscosity of red blood cell and attenuate the affect of low hematocrit on concentration determinations. Other test strips have included lysis agents and systems configured to determine hemoglobin concentration in an attempt to correct hematocrit. Further, biosensors have been configured to measure hematocrit by measuring optical variations after irradiating the blood sample with light, or measuring hematocrit based on a function of sample chamber fill time. These methods have the disadvantages of increasing the cost and complexity of test strips and may undesirably increase the time required to determine an accurate glucose measurement.

In addition, alternating current (AC) impedance methods have also been developed to measure electrochemical signals at frequencies independent of a hematocrit effect. Such methods suffer from the increased cost and complexity of advanced meters required for signal filtering and analysis.

Accordingly, systems and methods for determining analyte concentration are desired that overcome the drawbacks of current biosensors and improve upon existing electrochemical biosensor technologies.

SUMMARY OF THE INVENTION

Some embodiments of this invention are directed to methods and systems for determining a concentration of an analyte using one or more current decay curves. Other embodiments of this invention use two or more time segments from the current decay curves. Current decay curves can represent a gradual decrease in measured current response following application of a potential excitation to a biosensor containing a fluid sample. Fluid samples containing similar analyte concentrations but different sample matrix (e.g. different hematocrit values) can produce different current decay curves. However, these current decay curves were found to converge to a common value over time under certain conditions. Generally, fluid samples containing low analyte concentrations can converge faster than fluid samples containing high analyte concentrations. Based on this convergence behavior, an analyte concentration can be determined by dynamically selecting an appropriate time segment and a calibration curve associated with the selected time segment.

One embodiment consistent with the principles of this invention is a method for determining a concentration of an analyte described as follows. The steps include applying a potential excitation to a fluid sample containing an analyte, and determining if a current decay curve associated with the fluid sample has substantially entered an analyte depletion stage. The steps also include measuring a plurality of current values associated with the fluid sample during the analyte depletion stage, and calculating an analyte concentration based on at least one of the plurality of current values.

Another embodiment of this invention is directed to a system for determining an analyte concentration in a fluid sample. The system includes a set of electrodes positioned within a sample chamber and configured to apply a potential excitation to a fluid sample containing an analyte. The system also includes a sample chamber having a spacer height of less than about 110 μm and a processor configured to determine if a current decay curve associated with the fluid sample has substantially entered an analyte depletion stage. The processor is also configured to measure a plurality of current values associated with the fluid sample during the analyte depletion stage and calculate an analyte concentration based on at least one of the plurality of current values.

Another embodiment of this invention is directed to a biosensor. The biosensor includes a set of coplanar electrodes configured to apply a potential excitation to a fluid sample containing an analyte. Also, the biosensor has a sample chamber configured to receive the fluid sample and house the electrodes, wherein the sample chamber has a height above the electrodes of less than about 110 μm.

Additional embodiments consistent with principles of the invention are set forth in the detailed description which follows or may be learned by practice of methods or use of systems or articles of manufacture disclosed herein. It is understood that both the foregoing general description and the following detailed description are exemplary and explanatory only, and are not restrictive of the invention as claimed. Additionally, it is to be understood that other embodiments may be utilized and that electrical, logical, and structural changes may be made without departing form the spirit and scope of the present invention.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE EMBODIMENTS

Reference will now be made in detail to the present embodiments of the invention, examples of which are illustrated in the accompanying drawings. Wherever possible, the same reference numbers will be used throughout the drawings to refer to the same or like parts.

In accordance with an exemplary embodiment, a method of determining an analyte concentration is described. Many industries have a commercial need to monitor the concentration of particular analytes in various fluids. The oil refining industry, wineries, and the dairy industry are examples of industries where fluid testing is routine. In the health care field, people such as diabetics, for example, need to routinely monitor analyte levels of their bodily fluids using biosensors. A number of systems are available that allow people to test a physiological fluid (e.g. blood, urine, or saliva), to conveniently monitor the level of a particular analyte present in the fluid, such as, for example, glucose, cholesterol, ketone bodies, or specific proteins. Such systems can include a meter configured to determine the analyte concentration and/or display representative information to a user. In addition, such metering systems can incorporate disposable test strips configured for single-use testing of a fluid sample.

While such metering systems have been widely adopted, some are susceptible to inaccurate readings resulting from analyzing fluids of differing properties. For example, blood glucose monitoring using electrochemical techniques can be highly dependent upon hematocrit and/or temperature fluctuations. The present method reduces unwanted influences by applying a small potential excitation for a short period to the sample before applying a full potential excitation for an extended time period as occurs with traditional electrochemical systems. The ratio of current-transients measured shortly after the excitation pulses has been found to be generally independent of hematocrit and/or temperature fluctuations. Also, the ratio shows a generally linear relationship with analyte concentration, permitting an improved determination of analyte concentration. The present disclosure provides methods and systems for improved determination of analyte concentration.

Figure 1B:
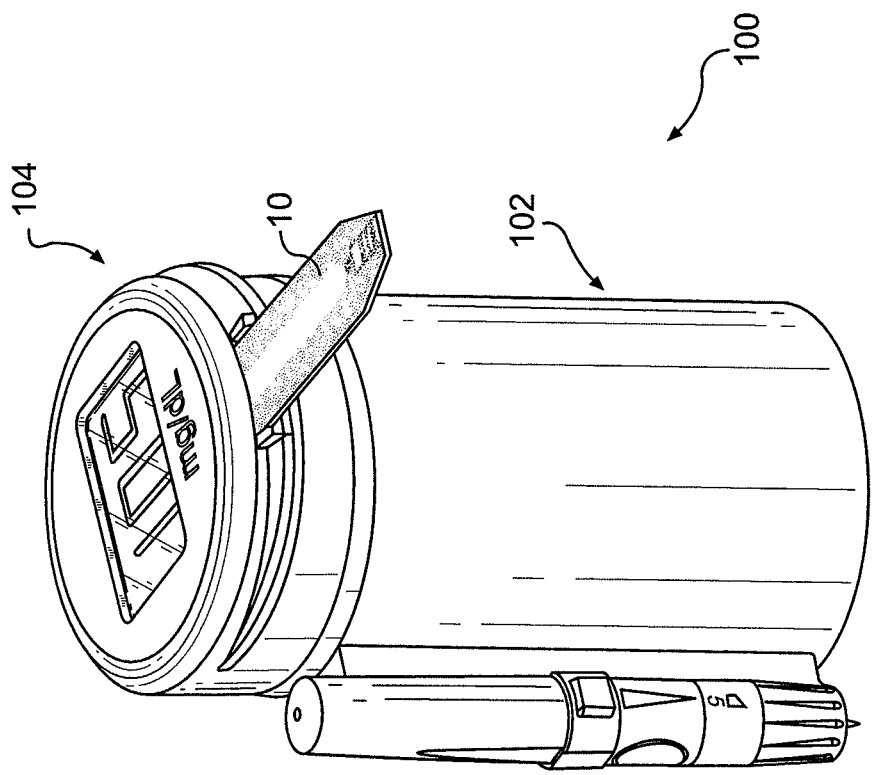
FIG. 1B illustrates a test meter that can be used with test media, according to an exemplary embodiment of the present disclosure.
Figure 1A:
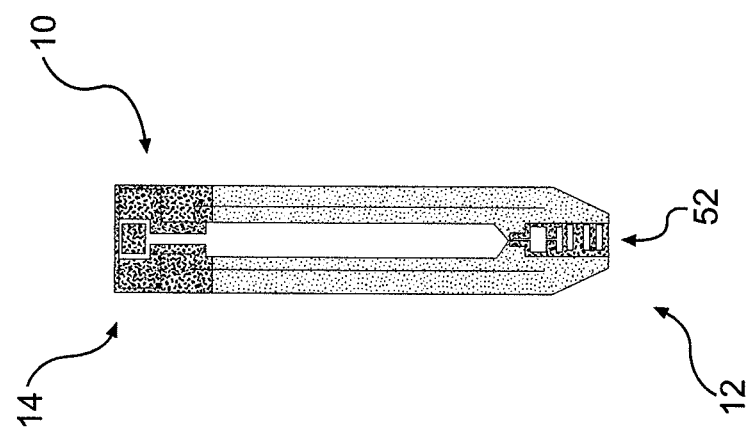
FIG. 1A illustrates test media associated with an exemplary meter system, according to an exemplary embodiment of the present disclosure.
Figure 1C:
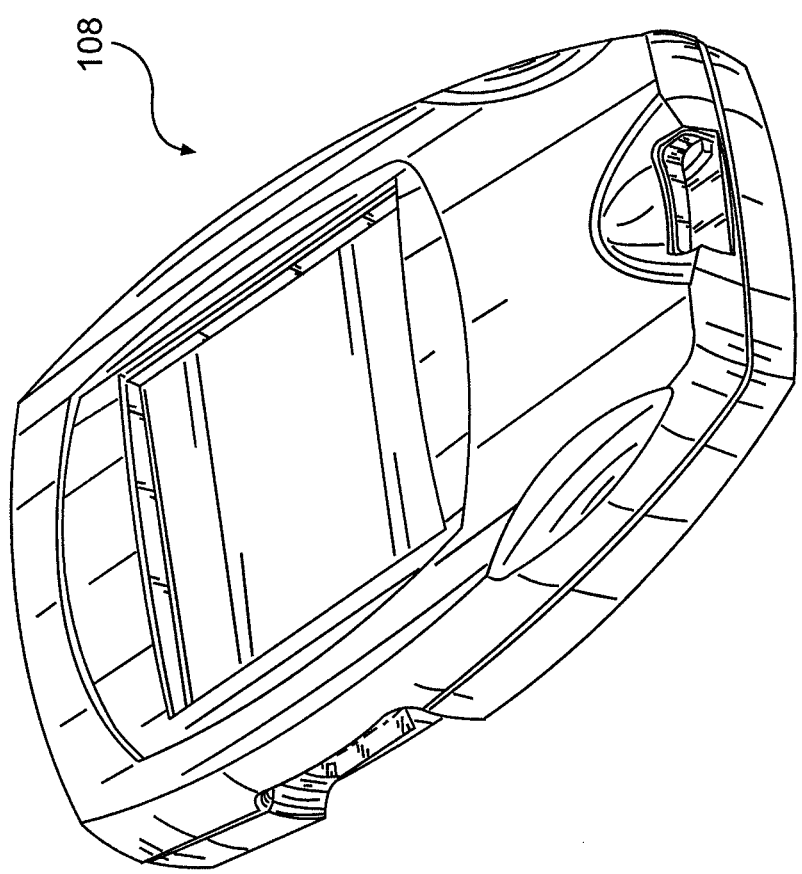
FIG. 1C illustrates another test meter that can be used with test media, according to an exemplary embodiment of the present disclosure.

FIG. 1A illustrates a diagnostic test strip 10, according to an exemplary embodiment of the present disclosure. Test strip 10 of the present disclosure may be used with a suitable test meter 100, 108, as shown in FIGS. 1B and 1C, configured to detect, and/or measure the concentration of one or more analytes present in a sample solution applied to test strip 10. As shown in FIG. 1A, test strip 10 can be generally planar and elongated in design. However, test strip 10 may be provided in any suitable form including, for example, ribbons, tubes, tabs, discs, or any other suitable form. Furthermore, test strip 10 can be configured for use with a variety of suitable testing modalities, including electrochemical tests, photochemical tests, electro-chemiluminescent tests, and/or any other suitable testing modality.

Test strip 10 can be in the form of a generally flat strip that extends from a proximal end 12 to a distal end 14. For purposes of this disclosure, "distal" refers to the portion of test strip 10 further from the fluid source (i.e. closer to the meter) during normal use, and "proximal" refers to the portion closer to the fluid source (e.g. a finger tip with a drop of blood for a glucose test strip) during normal use. In some embodiments, proximal end 12 of test strip 10 may include a sample chamber 52 configured to receive a fluid sample, such as, for example, a blood sample. Sample chamber 52 and test strip 10 of the present specification can be formed using materials and methods described in commonly owned U.S. Pat. No. 6,743,635, which is hereby incorporated by reference in its entirety.

Test strip 10 can be any convenient size. For example, test strip 10 can measure approximately 35 mm long (i.e., from proximal end 12 to distal end 14) and approximately 9 mm wide. Proximal end 12 can be narrower than distal end 14 in order to assist the user in locating the opening where the blood sample is to be applied. Further, test meter 100, 108 can be configured to operate with, and dimensioned to receive, test strip 10.

Test meter 100, 108 may be selected from a variety of suitable test meter types. For example, as shown in FIG. 1B, test meter 100 includes a vial 102 configured to store one or more test strips 10. The operative components of test meter 100 may be contained in a meter cap 104. Meter cap 104 may contain electrical meter components, can be packaged with test meter 100, and can be configured to close and/or seal vial 102. Alternatively, test meter 108 can include a monitor unit separated from storage vial, as shown in FIG. 1C. In some embodiments, meter 100 can include one or more circuits, processors, or other electrical components configured to perform one or more steps of the disclosed method of determining an analyte concentration. Any suitable test meter may be selected to provide a diagnostic test using test strip 10 produced according to the disclosed methods.

Test Strip Configuration

Figure 2A:
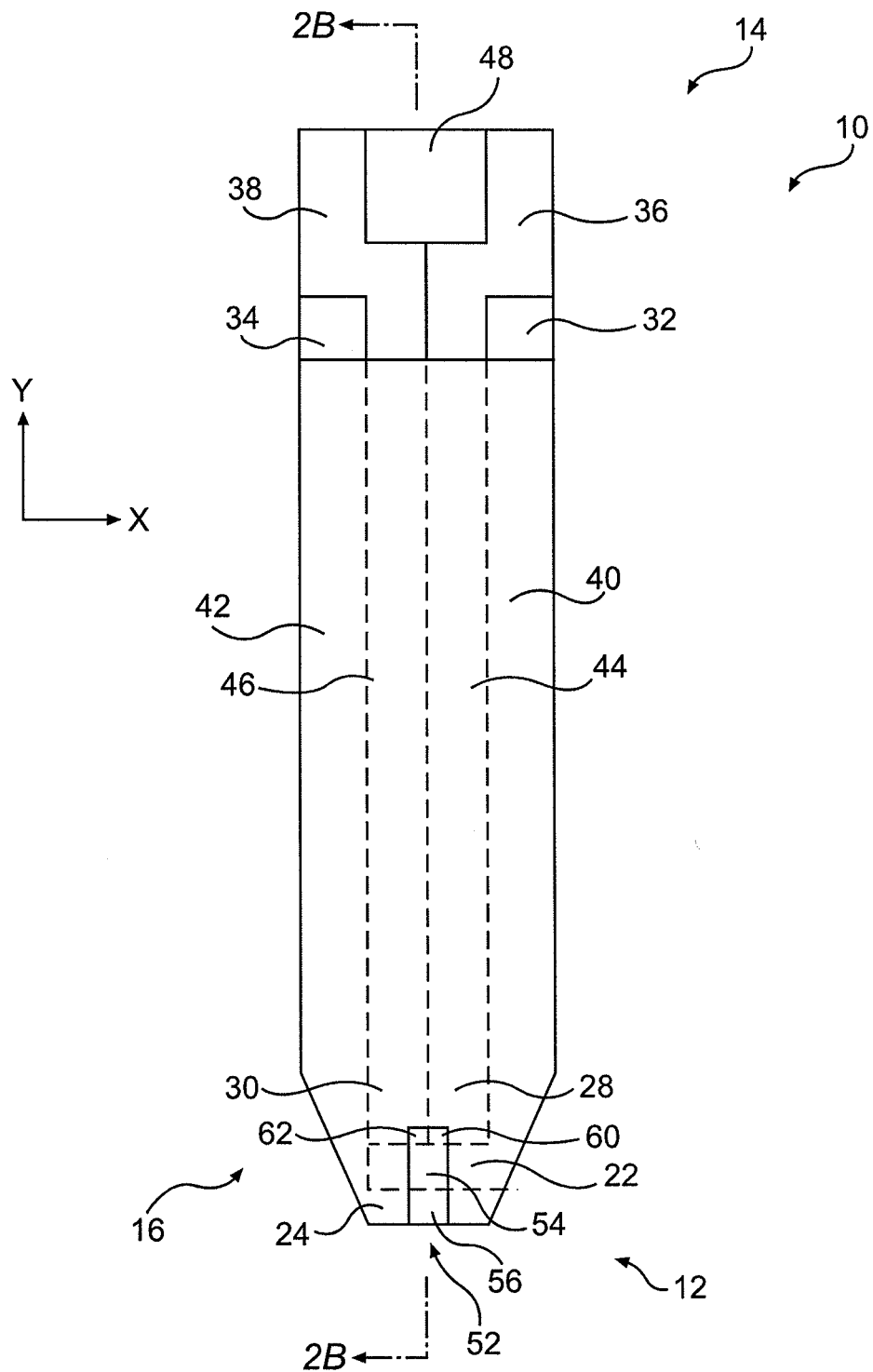
FIG. 2A is a top plan view of a test strip, according to an exemplary embodiment of the present disclosure.
Figure 2B:
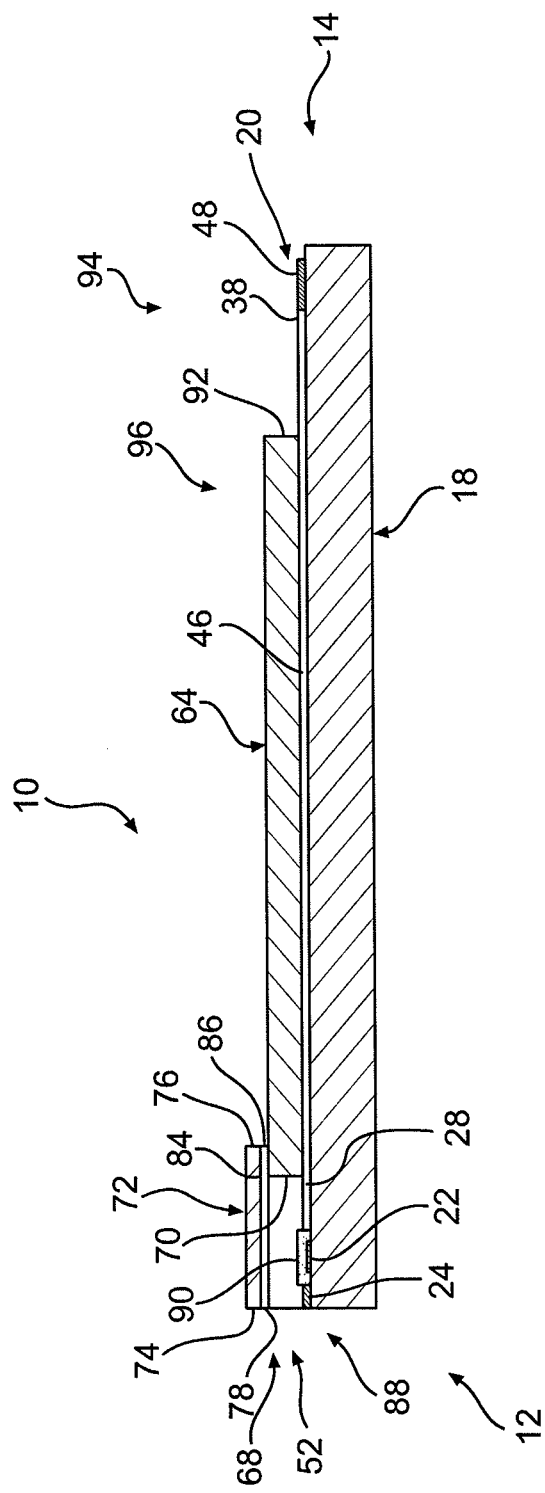
FIG. 2B is a cross-sectional view of the test strip of FIG. 2A, taken along line 2B-2B.

FIGS. 2A and 2B show a test strip 10, in accordance with an exemplary embodiment of the present disclosure. As shown in FIG. 2B, test strip 10 can include a generally layered construction. Working upwardly from the bottom layer, test strip 10 can include a base layer 18 extending along the entire length of test strip 10. Base layer 18 can be formed from an electrically insulating material that has a thickness sufficient to provide structural support to test strip 10. For example, base layer 18 can be a polyester material about 0.35 mm thick.

According to the illustrative embodiment, a conductive layer 20 can be disposed on base layer 18. Conductive layer 20 includes a plurality of electrodes disposed on base layer 18 near proximal end 12, a plurality of electrical contacts disposed on base layer 18 near distal end 14, and a plurality of conductive regions electrically connecting the electrodes to the electrical contacts. In the illustrative embodiment depicted in FIG. 2A, the plurality of electrodes includes a working electrode 22, a counter electrode 24, and a pair of fill-detect electrodes 28, 30. As described in detail below, the term "working electrode" refers to an electrode at which an electrochemical oxidation and/or reduction reaction occurs, e.g., where an analyte, typically the electron mediator, is oxidized or reduced. "Counter electrode" refers to an electrode paired with working electrode 22.

The electrical contacts at distal end 14 can correspondingly include a working electrode contact 32, a proximal electrode contact 34, and fill-detect electrode contacts 36, 38. The conductive regions can include a working electrode conductive region 40, electrically connecting working electrode 22 to working electrode contact 32, a counter electrode conductive region 42, electrically connecting counter electrode 24 to counter electrode contact 36, and fill-detect electrode conductive regions 44, 46 electrically connecting fill-detect electrodes 28, 30 to fill-detect contacts 36, 38. Further, the illustrative embodiment is depicted with conductive layer 20 including an auto-on conductor 48 disposed on base layer 18 near distal end 14.

In addition to auto-on conductor 48, the present disclosure provides test strip 10 that includes electrical contacts near distal end 14 that are resistant to scratching or abrasion. Such test strips can include conductive electrical contacts formed of two or more layers of conductive and/or semi-conductive material. Further, information relating to electrical contacts that are resistant to scratching or abrasion are described in co-owned U.S. patent application Ser. No. 11/458,298 which is incorporated by reference herein in its entirety.

The next layer of test strip 10 can be a dielectric spacer layer 64 disposed on conductive layer 20. Dielectric spacer layer 64 can be composed of an electrically insulating material, such as polyester. Dielectric spacer layer 64 can be about 0.100 mm thick and covers portions of working electrode 22, counter electrode 24, fill-detect electrodes 28, 30, and conductive regions 40-46, but in the illustrative embodiment does not cover electrical contacts 32-38 or auto-on conductor 48. For example, dielectric spacer layer 64 can cover substantially all of conductive layer 20 thereon, from a line just proximal of contacts 32 and 34 all the way to proximal end 12, except for sample chamber 52 extending from proximal end 12. In this way, sample chamber 52 can define an exposed portion 54 of working electrode 22, an exposed portion 56 of counter electrode 24, and exposed portions 60, 62 of fill-detect electrodes 28, 30.

In some embodiments, sample chamber 52 can include a first opening 68 at proximal end 12 of test strip 10, and a second opening 86 for venting sample chamber 52. Further, sample chamber 52 may be dimensioned and/or configured to permit, by capillary action, a blood sample to enter through first opening 68 and remain within sample chamber 52. For example, sample chamber 52 can be dimensioned to receive about 1 micro-liter or less. For example, first sample chamber 52 can have a length (i.e., from proximal end 12 to distal end 70) of about 0.140 inches, a width of about 0.060 inches, and a height (which can be substantially defined by the thickness of dielectric spacer layer 64) of about 0.005 inches. Other dimensions could be used, however.

A cover 72, having a proximal end 74 and a distal end 76, can be attached to dielectric spacer layer 64 via an adhesive layer 78. Cover 72 can be composed of an electrically insulating material, such as polyester, and can have a thickness of about 0.1 mm. Additionally, the cover 72 can be transparent. Adhesive layer 78 can include a polyacrylic or other adhesive and have a thickness of about 0.013 mm. A break 84 in adhesive layer 78 can extend from distal end 70 of first sample chamber 52 to an opening 86, wherein opening 86 can be configured to vent sample chamber 52 to permit a fluid sample to flow into sample chamber 52. Alternatively, cover 72 can include a hole (not shown) configured to vent sample chamber 52. It is also contemplated that various materials, surface coatings (e.g. hydrophilic and/or hydrophobic), or other structure protrusions and/or indentations at proximal end 12 may be used to form a suitable sample reservoir.

As shown in FIG. 2B, a reagent layer 90 can be disposed in sample chamber 52. In some embodiments, reagent layer 90 can include one or more chemical constituents to enable the level of glucose in the blood sample to be determined electrochemically. Reagent layer 90 may include an enzyme specific for glucose, such as glucose oxidase or glucose dehydrogenase, and a mediator, such as potassium ferricyanide or ruthenium hexamine. In other embodiments, other reagents and/or other mediators can be used to facilitate detection of glucose and other analytes contained in blood or other physiological fluids. In addition, reagent layer 90 may include other components, buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485). For example, an exemplary formulation contains 50-250 mM potassium phosphate at pH 6.75-7.50, 150-190 mM ruthenium hexamine, 3500-5000 U/mL PQQ-dependent glucose dehydrogenase, 0.5-2.0% polyethylene oxide, 0.025-0.20% NATROSOL 250M (hydroxyethylcellulose), 0.675-2.5% Avicel (microcrystalline cellulose), 0.05-0.25% TRITON-X (surfactant) and 2.5-5.0% trehalose.

In some embodiments, various constituents may be added to reagent layer 90 to at least partially reduce unwanted bias of an analyte measurement. For example, various polymers, molecules, and/or compounds may be added to reagent layer 90 to reduce cell migration and hence may increase the accuracy of a measurement based on an electrochemical reaction. Also, one or more conductive components may be coated with a surface layer (not shown) to at least partially restrict cell migration onto the one or more conductive components. These and other techniques known in the art may be used to reduce unwanted signal bias.

Although FIGS. 2A and 2B illustrate an illustrative embodiment of test strip 10, other configurations, chemical compositions and electrode arrangements could be used. For example, fill-detect electrode 30 can function with working electrode 22 to perform a fill-detect feature, as previously described. Other configurations of electrodes on test strip 10 are possible, such as, for example, a single fill-detect electrode, multiple fill-detect electrodes aligned in the y-axis (as opposed to the x-axis as shown in FIG. 2A), and/or multiple working electrodes.

In some embodiments, working electrode 22 and counter electrode 24 can be spaced further apart. For example, this electrode pair may be spaced at a distance of 500 µm to 1000 µm such that a two-pulse measurement obtained from the electrode pair can be optimized for correction of the influence of hematocrit, temperature, or other factors.

Test Strip and Meter Operation

As previously described, test strip 10 can be configured for placement within meter 100, or similar device, configured to determine the concentration of an analyte contained in a solution in contact with test strip 10. Meter 100 can include electrical components, circuitry, and/or processors configured to perform various operations to determine analyte concentration based on electrochemical techniques. For example, the metering system, such as meter 100 and associated test strip 10, may be configured to determine the glucose concentration of a blood sample. In some embodiments, systems and methods of the present disclosure permit determination of blood glucose levels generally unaffected by blood constituents, hematocrit levels, and temperature.

In operation, the battery-powered meter 100 may stay in a low-power sleep mode when not in use. When test strip 10 is inserted into meter 100, one or more electrical contacts at distal end 14 of test strip 10 could form electrical connections with one or more corresponding electrical contacts in meter 100. These electrical contacts may bridge electrical contacts in meter 100, causing a current to flow through a portion of the electrical contacts. Such a current flow can cause meter 100 to "wake-up" and enter an active mode.

Meter 100 can read encoded information provided by the electrical contacts at distal end 14. Specifically, the electrical contacts can be configured to store information, as described in U.S. patent application Ser. No. 11/458,298. In particular, an individual test strip 10 can include an embedded code containing data associated with a lot of test strips, or data particular to that individual strip. The embedded information can represent data readable by meter 100. For example, a microprocessor associated with meter 100 could access and utilize a specific set of stored calibration data specific to an individual test strip 10 and/or a manufactured lot test strips 10. Individual test strips 10 may be calibrated using standard solutions, and associated calibration data could be applied to test strips 10 of the same or similar lots of manufactured test strips 10.

In some embodiments, "lot specific" calibration information can be encoded on a code chip accompanying a vial of strips, or coded directly onto one or more test strips 10 manufactured in a common lot of test strips. Lot calibration can include any suitable process for calibrating test strip 10 and/or meter 100. For example, calibration can include applying at the factory a standard solution to one or more test strips 10 from a manufacturing lot, wherein the standard solution can be a solution of known glucose concentration, hematocrit, temperature, or any other appropriate parameter associated with the solution. Following application of the standard solution, one or more pulses can be applied to test strip 10, as described below. Calibration data may then be determined by correlating various measurements to be determined by the meter 100 during use by the patient with one or more parameters associated with the standard solution. For example, a measured current may be correlated with a glucose concentration, or a voltage correlated with hematocrit. Such calibration data, that can vary from lot to lot with the performance of the test strips, may then be stored on test strip 10 and/or meter 100, and used to determine analyte concentration of an analyte sample, as described below.

Test strip 10 can be tested at any suitable stage during a manufacturing process. Also, a test card (not shown) could be tested during any suitable stage of a manufacturing process, as described in co-owned U.S. patent application Ser. No. 11/504,710 which is incorporated by reference herein in its entirety. Such testing of test strip 10 and/or the test card can permit determination and/or encoding of calibration data at any suitable stage during a manufacturing process. For example, calibration data associated with methods of the present disclosure can be encoded during the manufacturing process.

In operation meter 100 can be configured to identify a particular test to be performed or provide a confirmation of proper operating status. Also, calibration data pertaining to the strip lot, for either the analyte test or other suitable test, could be otherwise encoded or represented, as described above. For example, meter 100 can identify the inserted strip as either test strip 10 or a check strip (not shown) based on the particular code information.

If meter 100 detects test strip 10, it may perform a test strip sequence. The test strip sequence may confirm proper functioning of one or more components of test strip 10. For example, meter 100 could validate the function of working electrode 22, counter electrode 24, and, if included, the fill-detect electrodes, by confirming that there are no low-impedance paths between any of these electrodes. If the electrodes are valid, meter 100 could provide an indication to the user that a sample may be applied to test strip 10.

If meter 100 detects a check strip, it may perform a check strip sequence. The system may also include a check strip configured to confirm that the instrument is electrically calibrated and functioning properly. The user may insert the check strip into meter 100. Meter 100 may then receive a signal from the check strip to determine if meter 100 is operating within an acceptable range.

In other embodiments, test strip 10 and/or meter 100 may be configured to perform a calibration process based on a standard solution, also termed a control solution. The control solution may be used to periodically test one or more functions of meter 100. For example, a control solution may include a solution of known electrical properties, and an electrical measurement of the solution may be performed by meter 100. Upon detecting the presence of a control solution, meter 100 can perform an operational check of test strip 10 functionality to verify measurement integrity. For example, the read-out of meter 100 may be compared to a known glucose value of the solution to confirm that meter 100 is functioning to an appropriate accuracy. In addition, any data associated with a measurement of a control solution may be processed, stored or displayed using meter 100 differently to any data associated with a glucose measurement. Such different treatment of data associated with the control solution may permit meter 100, or user, to distinguish a glucose measurement, or may permit exclusion of any control measurements when conducting any mathematical analysis of glucose measurements.

Analyte Concentration Determination

Meter 100 can be configured to apply a signal to test strip 10 to determine a concentration of an analyte contained in a solution contacting test strip 10. In some cases, the signal can be applied following a determination that sample chamber 52 of test strip 10 contains a sufficient quantity of fluid sample. To determine the presence of sufficient fluid, meter 100 can apply a detect voltage between any suitably configured electrodes, such as, for example, fill-detect electrodes. The detect voltage can detect the presence of sufficient quantity of fluid (e.g. blood) within sample chamber 52 by detecting a current flow between the fill-detect electrodes. In addition, to determine that the fluid sample has traversed reagent layer 90 and mixed with the chemical constituents in reagent layer 90, meter 100 may apply a fill-detect voltage to the one or more fill-detect electrodes and measure any resulting current. If the resulting current reaches a sufficient level within a predetermined period of time, meter 100 can indicate to a user that adequate sample is present. Meter 100 can also be programmed to wait for a predetermined period of time after initially detecting the blood sample to allow the blood sample to react with reagent layer 90. Alternatively, meter 100 can be configured to immediately begin taking readings in sequence.

Meter 100 can be configured to apply various signals to test strip 10. For example, an exemplary fluid measurement sequence could include amperometry, wherein an assay voltage is applied between working and counter electrodes 22, 24 of test strip 10. The magnitude of the assay voltage can include any suitable voltage, and could be approximately equal to the redox potential of constituents of reagent layer 90. Following application assay voltage, also termed potential excitation, meter 100 could be configured to measure one or more current values between working and counter electrodes 22, 24. Such a measured current can be mathematically related to the concentration of analyte in the fluid sample, such as, for example, glucose concentration in a blood sample.

For example, one or more constituents of reagent layer 90 may react with glucose present in a blood sample such that glucose concentration may be determined using electrochemical techniques. Suitable enzymes of reagent layer 90 (e.g. glucose oxidase or glucose dehydrogenase) could react with blood glucose. Glucose could be oxidized to form gluconic acid, which may in turn reduce a suitable mediator, such as, for example, potassium ferricyanide or ruthenium hexamine. Voltage applied to working electrode 22 may oxidize the ferrocyanide to form ferricyanide, and generating a current proportional to the glucose concentration of the blood sample.

As previously discussed, measurements of analyte concentration using a biosensor may be inaccurate due to unwanted effects of various blood components. For example, the hematocrit level (i.e. the percentage of blood occupied by red blood cells) of blood can erroneously affect a measurement of analyte concentration. In order to reduce any inaccuracies associated with determining analyte concentration, it may be advantageous to use multiple sets of calibration information. Such multiple calibration information can reduce errors due to hematocrit and other factors that may adversely affect analyte concentration determination.

In some embodiments, a potential excitation can be applied to a fluid sample in contact with test strip 10. An applied potential can include any suitable voltage signal, such as, for example, signals with constant, variable, or pulse-train voltages. Meter 100 may then measure a current value associated with the potential excitation, as previously described.

In some embodiments, a current may be measured at one or more time-points. A time-point can include a discrete time following application of a potential excitation. For example, a first current can be measured at a first time-point of 0.1 seconds, and a second current can be measured at a second time-point 0.2 seconds. The first time-point can occur 0.1 seconds following the application of the potential, and the second time-point can occur 0.2 seconds following the application of the potential. In some cases, a plurality of current values can be measured at any number of time-points following the application of a potential excitation.

Time-points can include irregular or regular time periods, and can include any suitable sampling rate. For example, the sampling rate could be 10 Hz, and in other embodiments the sampling rate could be 0.1, 1, 100, or 1000 Hz. In other embodiments, time-points could be sampled at non-constant sampling rates. For example, time-points could be sampled at increasing, decreasing, or non-uniform sampling rates.

In some embodiments, current values can be measured over a plurality of time-segments, wherein a time-segment can include, or span, a series of time-points. For example, a first time-segment could include any number of time-points up to four seconds, and a second time-segment could include any number of time-points between four and six seconds. Current values measured in the first time-segment could include one or more currents measured at 0.1, 0.2, 1.6, 2.0, 3.4, or 3.99 seconds, or at any other suitable times. Current values measured in the second time-segment could include one or more currents measured at 4.2, 4.63, 5.0, or 5.97 seconds, or at any other suitable times.

These one or more current values measured within different time-segments can then be used to determine analyte concentration based on calibration information associated with the different time-segments. For example, a low analyte concentration can be determined at an early time-segment, such as a first time-segment, based on calibration information associated with the low analyte concentration. Conversely, a high analyte concentration can be determined at a later time-segment, such as a second time-segment, based on calibration information associated with the higher analyte concentration.

Various other calibration information can be associated with other time-segments. For example, in some embodiments the calibration information can be described by a calibration curve, wherein each time-segment can be associated with a particular calibration curve. A first calibration curve, associated with a first time-segment, can be used to determine analyte concentration if the measured current value is associated with the first time-segment. Alternatively, if the measured current value is associated with a second time-segment, a second calibration curve, associated with a second time-segment, can be used to determine analyte concentration. In some embodiments, three, four, or more, calibration curves can be used to determine analyte concentration, wherein each calibration curve is associated with a corresponding number of time-segments. In other embodiments, the range of one or more time-segments may overlap. For example, a first time-segment could include zero to four seconds and a second time-segment could include three to six seconds.

Exemplary embodiments disclosed herein use multiple sets of calibration information to permit more precise determinations of analyte concentration over a wider range of analyte concentrations than can be achieved using traditional techniques. In particular, different calibration curves can be associated with different ranges of analyte concentrations. The influence of hematocrit, temperature, blood constituents, and other factors that may adversely affect determination of blood glucose concentration can be reduced using techniques that employ multiple calibration curves. For example, the precision and/or accuracy of monitoring blood glucose levels using biosensors may be improved using the method or systems of the present disclosure. Two embodiments of the present invention will now be discussed in detail.

One exemplary embodiment is a method that includes calculating an analyte concentration based on a measured current and a calibration curve dynamically selected from a plurality of calibration curves. The plurality of calibration curves can associated with a plurality of time-segments such that a single calibration curve can be associated with a single time-segment. For example, at a time-point within the first time-segment, the analyte concentration can be calculated using parameters associated with the first time-segment calibration curve. If the calculated analyte concentration is within a pre-determined concentration range associated with the first time-segment, current measurement can stop, analyte concentration can be determined and the result displayed. If the calculated analyte concentration is outside the pre-determined range, the current measurement can continue to a time-point within a second time-segment. At a time-point within the second time-segment, the analyte concentration can be calculated using the parameters associated with a second calibration curve. If the calculated analyte concentration is within a pre-determined concentration range associate with the second time-segment, current measurement can stop, analyte concentration can be determined and the result displayed. Otherwise, the measurement can continue to another time-point within a third time-segment. This process can be repeated such that the entire measurement range can be covered if required. Such a method permits selection of a suitable calibration curve based on time, or time-related information. Such a dynamic selection process could also be applied to ranges of current values, associated analyte concentrations, or other parameters associated with the electrochemical technique used to determine analyte concentration.

Figure 3:
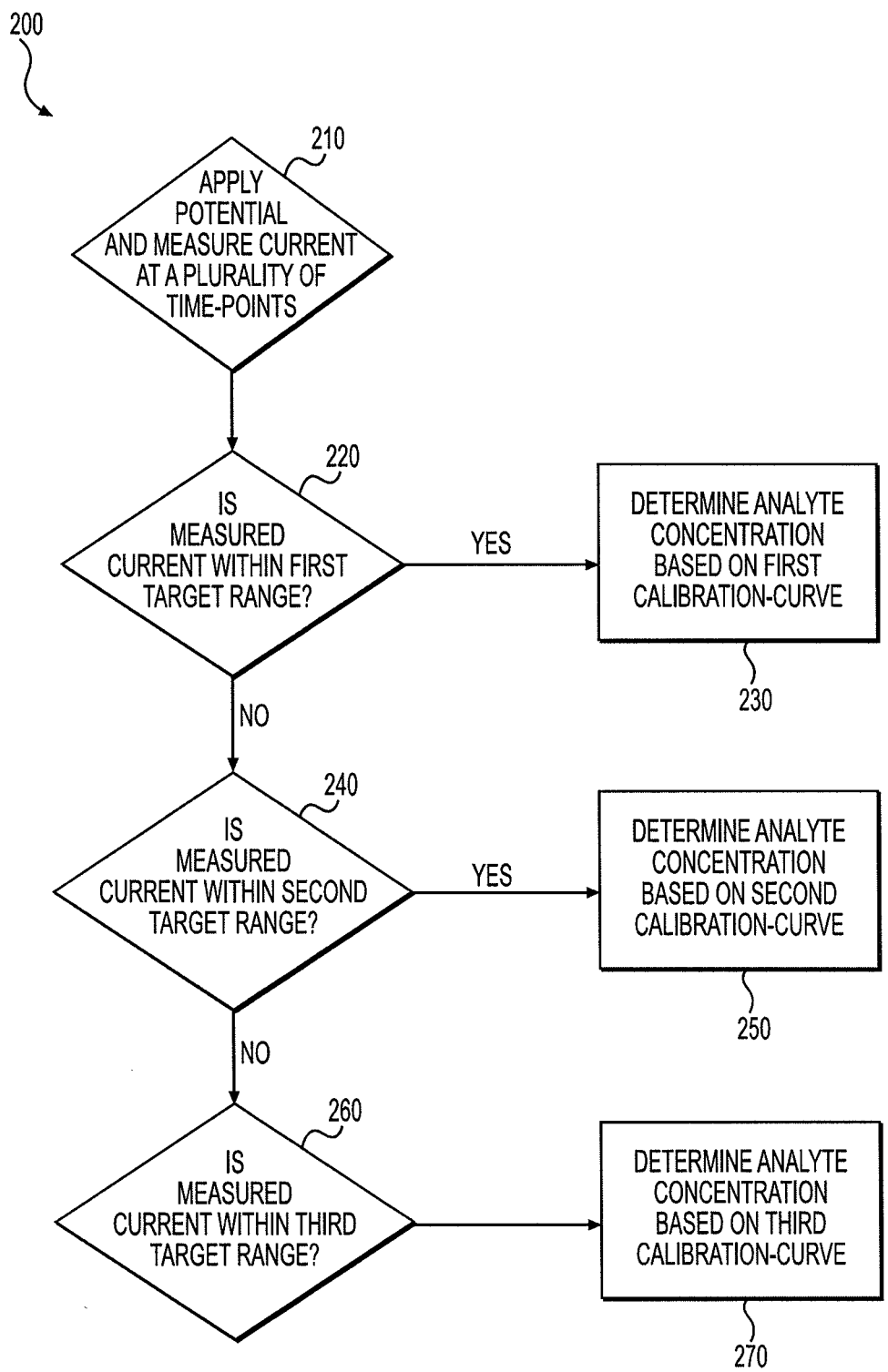
FIG. 3 depicts flow chart of a method of determining an analyte concentration, according to an exemplary embodiment of the present disclosure.

FIG. 3 depicts a method 200 for determining analyte concentration, according to an exemplary embodiment of the present disclosure. As described above, a potential excitation can be applied to a fluid sample contained within test strip 10. Meter 100 can be configured to measure an associated current at a plurality of time-points, wherein the measured current can result from the application of a potential excitation across electrodes 22, 24. Meter 100 may then determine a blood glucose level based on multiple calibration information associated with various time-segments.

In some embodiments, method 200 can include measuring a current value at a plurality of time-points (Step 210). Each measured current value can be associated with a specific time-point, such as, for example, 0.1, or 0.2 seconds, as described above. These current values can be stored in memory as required by the various circuits or processors of meter 100. Some processors may include internal memory sufficient to at least temporarily store one or more measured currents. Other processes may interact with one or more memory systems configured to at least temporarily store one or more measured currents. Various storage systems may be located within meter 100, test strip 10, or later developed.

Following application of a potential excitation and a current measurement, an analyte concentration may be determined based on the measured current and a suitable calibration curve. In particular, at a time-point following the application of a potential excitation, a current measurement can be obtained. This current measurement can then be compared to a current associated with a known analyte concentration. If the current values are approximately equal, then the unknown analyte concentration should be approximately equal to the known analyte concentration. The actual value of the analyte concentration can then be determined based on a calibration curve associated with the known analyte concentration.

The known analyte concentration can be associated with a known current value and a specific time-segment. Generally, lower analyte concentrations are associated with earlier time-segments, and higher analyte concentrations are associated with later time-segments, as explained above. These various calibration curves, known current values, time-segments, and other data can be determined empirically and can vary depending on test strip and meter design, manufacturing conditions, fluid type, operating conditions, etc.

In some embodiments, a measured current can be compared with a target-range of analyte concentrations. The target-range could include known ranges of analyte concentrations. For example, four target-ranges could encompass of range of glucose concentrations. A first target-range could be about 10 to about 50 mg/dL, a second target-range could be about 50 to about 150 mg/dL, a third target-range could be about 150 to about 350 mg/dL, and a fourth target-range could be about 350 to about 600 mg/dL. Any other number or values of target-ranges could also be used.

As an initial step, a measured current can be compared to a current associated with a first time-segment, such as a first target-range (Step 220). For example, if a measured current is within a range of currents associated with a first target-range, analyte concentration can be determined based on a first calibration curve (Step 230). Alternatively, if a measured current is outside a range of currents associated with the first target-range, analyte concentration can be determined based on another calibration curve.

The first calibrated-curve could include any suitable calibration information associated with a first time-segment. For example, a first calibrated-curve can correspond to an analyte concentration between a lower and an upper analyte concentration. Such an association can permit use of concentration-dependent calibration information. For example, one set of calibration information may exist for low analyte concentrations while another set of calibration information may exist for high analyte concentrations. In some embodiments, two, three, four or more different calibration curves could be used to correspond to a range of analyte concentrations.

Each calibration curve could include empirical data associated with a range of analyte concentrations, termed "calibration-range." In some embodiments, the calibration-range may be different to the corresponding target-range. For example, a first target-range may be about 10 to 50 mg/dL, while a first calibration-range may be about 0 to 75 mg/dL. A calibration-range larger than the corresponding target-range can permit greater accuracy in determining the corresponding calibration curve as a greater range of empirical data can be used to determine the calibration curve. Also, as explained in detail below, adjacent calibration-ranges can overlap and provide additional data for determining a calibration curve.

In some embodiments, four calibration-ranges can be used to determine four calibration curves. For example, a first calibration-range can be about 0 to about 75 mg/dL, a second calibration-range can be about 30 to about 240 mg/dL, a third calibration-range can be about 75 to about 450 mg/dL, and a fourth calibration-range can be about 240 to about 600 mg/dL. Also, each particular calibration curve can be associated with a corresponding calibration-range such that a first calibration curve is associated with a first calibration-range, a second calibration curve is associated with a second calibration-range, and so forth.

Figure 4:
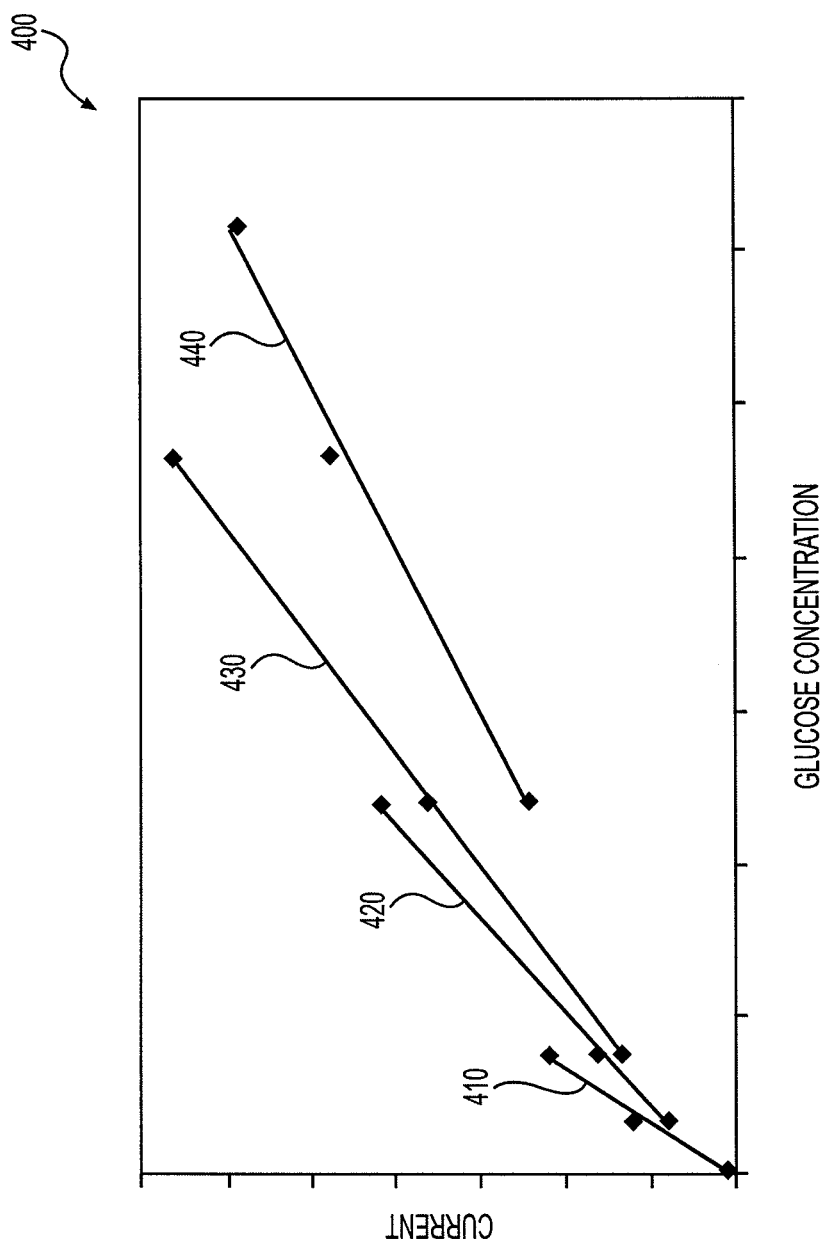
FIG. 4 depicts a plurality of calibration curves on a graph of current versus glucose concentration, according to an exemplary embodiment of the present disclosure.

For example, FIG. 4 depicts a chart 400 representing calibration data for a test strip and meter configured to determine glucose concentration using four time-segments. A first calibration curve 410 associated with a first time-segment can be determined using a first calibration-range of glucose concentrations, such as, for example, 0 to 75 mg/dL. A second calibration curve 420 associated with a second time-segment can be determined using a second calibration-range of glucose concentrations, such as, for example, 30 to 240 mg/dL. A third calibration curve 430 associated with a third time-segment can be determined using a third calibration-range of glucose concentrations, such as, for example, 75 to 450 mg/dL. A fourth calibration curve 440 associated with a fourth time-segment can be determined using a fourth calibration-range of glucose concentrations, such as, for example, 240 to 600 mg/dL.

As shown in FIG. 4, calibration curves 410, 420, 430, and 440 are generally linear and have different slopes. In other embodiments, such curves may not be generally linear, and may not have different slopes. For example, various curves could include quadratic, polynomial, data-fitted or other mathematical descriptions. Also, one or more calibration curves may have similar slopes.

Calibration curves can include any suitable representation of calibration information, such as, for example, slopes, relationships, charts, tables, equations, algorithms, or data formats. Calibration information can include strip, lot, or meter specific information, and can account for hematocrit, temperature, pH, or other variations in testing conditions, analyte type, or physiological sample. Such calibration information may be encoded on strip 10 and/or within meter 100.

In some embodiments, a comparison can include determining a difference between a measured current value and a current value associated with a known analyte concentration or range of analyte concentrations. For example, if the difference between the measured values is within a particular range, then method 200 may perform a specific step, such as determining an analyte concentration based on a particular calibration curve.

The event triggering the comparison between measured current and a current associated with a specific target-range of analyte concentrations could be any suitable event. In some embodiments, a period of time could elapse from the application of the excitation potential. For example, once the first time-segment is reached, such as four seconds, the comparison could be triggered. In other embodiments, a current reading could trigger the event. For example, a comparison could be triggered if a measured current drops below 3 mA. Certain values, or value ranges, of voltage, impedance, or other parameters associated with various electrochemical techniques could also be used as a triggering event.

As shown in method 200, if the measured current is outside the range of currents associated with the first target-range, then method 200 could continue. Specifically, additional current measurements can be sampled at increasing time-points from the application of the potential excitation. This could continue until a second time-segment is reached, such as, for example, six seconds. In other embodiments, a measured current value could be compared with a range of currents associated with a second target-range (Step 240). As previously described for the Step 220, if a measured current is within a range of currents associated with the second target-range, analyte concentration can be determined based on a second calibration curve (Step 250). Alternatively, if a measured current is outside a range of currents associated with the second target-range, analyte concentration can be determined based on another calibration curve.

In some embodiments, a series of currents measured at different time-points could also be used to determine analyte concentration. For example, if the second time-segment is 6 seconds, the series of measured currents, termed "time-currents," could include currents measured at 5.7, 5.8, 5.9 seconds, at a time-point sampling rate of 0.1 seconds. The time-currents could also include currents measured at 6.1, 6.2, 6.3, and so on. The time-currents measured during, prior to, or following, any time-segment could be used to determine analyte concentration via slope or other relationship data incorporating both the measured current and the time-current values.

Time-currents can be used to obtain slope and other relationship data associated with a particular time-segment. For example, slope data can be used to improve the precision of analyte concentration determination by providing another method to determine an analyte concentration other than relying solely on a measured current value. Slope data can also be used to determine an predicted current value at a later time-point, as discussed in detail below.

Time-currents can also be used to determine a current decay. The current decay can be based on the difference between a first current value and a second current value, and the difference between a first time-point and a second time-point, wherein the first current value can be measured at the first time-point and the second current value can be measured at the second time-point. Current decay can be used to improve the precision of analyte concentration determination by providing another method to determine an analyte concentration other than relying solely on a measured current value.

Returning to FIG. 3, following comparison of current values associated with the second target-range (Step 240), method 200 can determine if the measured current value is within a current range associated with a third target-range (Step 260). If within the third target-range, method 200 can determine analyte concentration using a third calibration curve (Step 270). If the difference in values is outside the range, method 200 can continue to sample additional time-points.

In some embodiments, a third time-segment can be nine seconds. Similar to Steps 220 and 240, Step 260 can determine if the measured current is within the third target-range. For example, the third target-range could be associated with a glucose concentration of about 350 mg/dL.

In some embodiments, method 200 can be applied to two, three or more time-segments associated with different ranges of analyte concentrations. For example, a fourth time-segment could be triggered at about fourteen seconds, or could be associated with a glucose concentration of about 600 mg/dL. If the difference between the values is not within the third variance range, method 200 could determine analyte concentration or could continue to a forth time-segment (not shown).

Another embodiment consistent with the principles of this invention extrapolates a current decay measured up to the first time-point to determine a current value at much longer time. This can be achieved by formulating an extrapolation algorithm using experimental data at longer test times. The extrapolated current, or "predicted current," can be correlated to analyte concentration with improved accuracy and precision. If the calculated analyte concentration is outside a predetermined range, the measurement continues to the second time-segment, similar to the method previously described. The extrapolation algorithm and analyte concentration determination can be determined using any number of calibration curves, as previously described. Further, this method can be repeated until the entire measurement range is covered.

Figure 5:
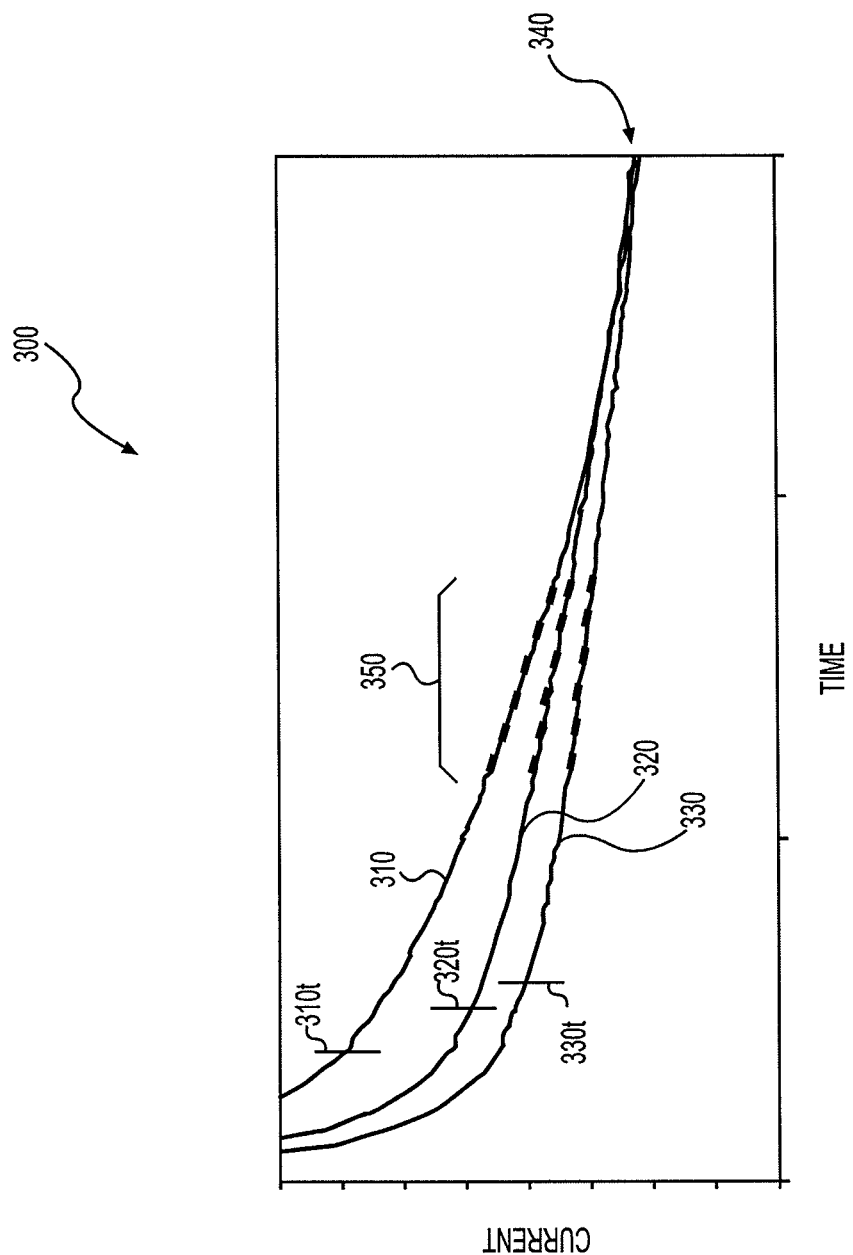
FIG. 5 depicts a plurality of current decay curves on a graph of current versus time, according to an exemplary embodiment of the present disclosure.

FIG. 5 depicts a chart 300 of three different fluid samples showing current decay curves over time after the application of a potential excitation. While the three samples depicted contain similar glucose concentrations, all three samples contain different amounts of red blood cells, i.e. different hematocrit values. The sample with the lowest hematocrit value is depicted by a line 310, and has the steepest slope over an indicated dashed range 350. In contrast, the sample with the highest hematocrit value is depicted by a line 330, and has the flattest slope over indicated range 350. A line 320 represents a sample with an intermediate hematocrit value. As shown, all three lines 310, 320, 330 approximately converge toward a generally common current value at a future time-point, as depicted by a region 340.

In some embodiments, glucose concentration can affect the shape of a current decay curve. For example, different hematocrit values can affect the convergence of current decay curves. In particular, samples containing lower glucose concentrations may reach a generally common current value faster than samples containing higher glucose concentrations. As such, current decay curves representing samples containing lower glucose concentrations may converge in a shorter time period than samples containing higher glucose concentrations. Determining a wide range of glucose concentrations could require two or more time segments, and calibration parameters associated with different time segments may be different.

In another embodiment, extrapolation techniques could be applied to one or more time segments of one or more current decay curves to determine a generally common current value that could be reached at a longer time. For example, data associated with slope information of a single decay curve could be used to determine a future current value or associated time value. Data contained within dashed range 350 could be extrapolated, using linear or other curve fitting techniques, to determine a current associated with region 340. Such a technique offers another method of determining glucose concentration within a shorter test time. Also, such slope or other relational data could be used in association with any one or more time-segments.

To determine slope information associated with a current decay curve, current data from two or more current measurements associated with two time-points may be obtained as previously described. These current data may then be fit with appropriate mathematical equations configured to provide a predicted current value at some future time-point. For example, an illustrative method could include measuring a first current value associated with the potential excitation at a first time-point and measuring a second current value associated with the potential excitation at a second time-point. The method could then determine a predicted current at a future time-point, wherein the predicted current could be determined using an extrapolated current decay curve based on the first and second current values. Analyte concentration could then be calculated based on the predicted current and a dynamically-selected calibration curve, as described above.

In some embodiments, the extrapolated current decay curve could be selected from a plurality of extrapolated current decay curves. These extrapolated current decay curves could be based on empirical data, or obtained using any suitable method known in the art. Such current decay curves may also be associated with one or more time-segments, analyte concentrations, or other parameters previously discussed.

Mechanism of Current Decay

As shown in FIG. 5, blood samples having different hematocrit values display different current decay curves. Generally, blood samples with lower hematocrit (i.e., low cellular concentration, line 310) display faster decay than blood samples with higher hematocrit (i.e., high cellular concentration, line 330). These different current decay properties between high and low hematocrit samples may be explained by two mechanisms underlying the current decay process.

Current decay can occur in two or more stages. A first stage can be generally "diffusion controlled," and may be described by the Cottrell equation:

$$i(t) = nFAC\sqrt{\frac{D}{\pi \cdot t}}$$

where i(t) represents the current measured at time t, n represents the number of electrons in the electrochemical reaction, F represents the Faraday constant, A represents the electrode surface area, C represents the concentration of electroactive species, and D represents the diffusion constant of the electroactive species.

At some point, current decay can show a transition from a first stage of decay to a second stage of decay. For example, a transition from a first "diffusion controlled" stage to a second "analyte depletion" stage can be dependent on the analyte concentration, hematocrit value of the sample, viscosity of the sample, or test time. As shown in FIG. 5, low hematocrit (line 310) can transition at point 310t, medium hematocrit (line 320) can transition at point 320t, and high hematocrit (line 330) can transition at point 330t. By way of example, a sample containing about 75 gm/dL of glucose, at about 25% to about 55% hematocrit, can transition to a second stage at about 7 seconds.

Following the transition into the second stage, current decay can be generally controlled by depletion of an electroactive species. This process can be analogous to a thin-layer electrochemical cell at a longer measurement time. In some embodiments, the current decay function during the "analyte depletion" stage can be described by an equation derived by Bard & Faulkner (A. J. Bard, L. R. Faulkner, *Electrochemical Methods*, John Wiley & Sons, N.Y. (1980)):

$$i(t) \approx i(0)\exp(-pt)$$

where i(t) represents the current measured at time t, i(0) represents an extrapolated current at time 0, and p represents a constant which is a function of diffusion coefficient and thickness of the electrochemical cell.

As shown in FIG. 5, current decay curves in the second "analyte depletion" stage can show convergence at different hematocrit levels to a common value (region 340). Convergence can occur in part because current decay at low hematocrit (i.e., line 310), representing a low viscosity sample, can exhibit a faster decay rate than samples of high hematocrit. Current decay at high hematocrit (i.e., line 330), representing a high viscosity sample, can exhibit a slower decay rate than samples of low hematocrit. As such, current decay curves for samples at different hematocrit levels with similar analyte concentration can converge to a similar current value. For example, lines 310, 320, and 330 show convergence at region 340.

Diffusion Layer Thickness

As outlined above, current decay can occur in at least two stages, one being "diffusion controlled," and one being "analyte depletion" controlled. The transition between these two stages can be determined by the relative magnitude of a diffusion layer thickness and a sample fluid thickness. The diffusion layer thickness at a given measurement time, δ(t) can be described by:

$$\delta(t) = \sqrt{2Dt}$$

where t represents a measurement time and D represents a diffusion constant of the electroactive species.

During two different stages of current decay, diffusion layer thickness generally increases with increasing time. As such, during "diffusion controlled" decay, the value of diffusion layer thickness can be less than a thickness of sample fluid contacting an electrode, such as, for example, the counter electrode or working electrode. Stated other ways, the diffusion layer thickness can be less than a height of a sample chamber, or "spacer thickness," wherein the spacer thickness defines the thickness of fluid sample above electrode surface. As such, "spacer thickness" can include a depth of fluid sample adjacent to an electrode, a height of spacer layer 64, a sample chamber height above an electrode, or other similar dimension. However, during an "analyte depletion" stage of current decay, the "diffusion layer thickness" value can become greater than sample fluid thickness or the spacer thickness.

Based on this understanding, the time to transition from a first to a second stage of current decay can be reduced by reducing the height of a sample chamber. Also, the transition time can be reduced by using a mediator with a higher diffusion coefficient. Either technique, alone or in combination, can reduce the time taken to reach an "analyte depletion" stage, where samples containing different hematocrits show current decay convergence. Therefore, reducing the height of a sample chamber or using a mediator with a higher diffusion coefficient can decrease a glucose measurement time with the effect of hematocrit convergence.

Current glucose test strips on the market have sample chamber heights in the range of about 113 μm to about 258 μm. In some embodiments, the sample chamber height of the current disclosure can be less than about 110 μm. In other embodiments, the sample chamber height can be less than about 100 μm. In yet other embodiments, the sample chamber height can be less than about 90 μm.

Because of the mechanism of hematocrit convergence, variation of spacer height from one test strip to another can affect the transition time and test results. The spacer height of an individual test strip or a number of test strips from different lots, can vary. To improve test results, the variability of these spacer heights should be controlled. For example, a spacer height can vary by less than 8 μm within a strip lot to achieve a coefficient of variation of less than 5%. In some embodiments, a spacer thickness, spacer height, or the height of a sample chamber can have a standard deviation of less than about 4 μm.

For example, an electroactive species may include ruthenium hexamine chloride, which has an associated diffusion coefficient of about $9.1 \times 10^{-6}$ cm$^2$/sec. While diffusion coefficients are generally provided for aqueous samples, the diffusion layer thickness values for blood samples may be lower than predicted. For ruthenium hexamine, the diffusion layer thickness may vary over time as shown below.

| Segment | Test Time (sec) | Diffusion Layer Thickness (μm) |
|---------|-----------------|-------------------------------|
| 1       | 4               | 85                            |
| 2       | 7               | 113                           |
| 3       | 10              | 135                           |

If a biosensor utilizing ruthenium hexamine has a sample chamber height of less than about 110 μm, a measurement during Segment 1 (i.e., less than four seconds) would be generally diffusion controlled. Alternatively, a measurement during Segment 2 or 3 would be generally controlled by "analyte depletion." Accordingly, hematocrit convergence would generally occur after about four seconds. However, if a sample chamber height were reduced to about 85 μm, hematocrit convergence could occur before four seconds during Segment 1.

In another example, the electroactive species may include potassium ferricyanide, which has an associated diffusion coefficient of about $0.58 \times 10^{-5}$ cm$^2$/sec. For potassium ferricyanide, the diffusion layer thickness may vary over time as shown below.

| Segment | Test Time (sec) | Diffusion Layer Thickness (µm) |
| --- | --- | --- |
| 1 | 4 | 71 |
| 2 | 7 | 94 |
| 3 | 10 | 112 |

If a biosensor utilizing potassium ferricyanide has a sample chamber height of less than about 110 µm, a measurement during Segment 1 or 2 (i.e., less than ten seconds) would be generally diffusion controlled. Alternatively, a measurement during Segment 3 would be generally controlled by "analyte depletion." Accordingly, hematocrit convergence would generally occur after about ten seconds. However, if a sample chamber height were reduced to about 94 µm, hematocrit convergence could occur before seven seconds during Segment 2.

The total time taken to measure a glucose concentration can be reduced by reducing the spacer height of the sample chamber because the time taken to reach hematocrit convergence ("analyte depletion" stage) can be decreased. Thus, the overall time taken to determine a hematocrit bias of a sample and then accurately measure a glucose concentration can be reduced.

In some embodiments, spacer height can be reduced by reducing the height of spacer layer 64, as shown above in FIG. 2B. Reducing the height of spacer layer 64 can reduce the height of sample chamber 52. Also, the internal dimension of a sample chamber can be modified. For example, the thickness of one or more electrodes may be selectively increased or the surface opposing an electrode may be coated.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for determining a concentration of an analyte in a fluid sample, the steps comprising:
applying a potential excitation to the fluid sample;
measuring a plurality of first current values during a first time-segment following application of the potential excitation, wherein a first set of calibration data is derived from the first time-segment and a second set of calibration data is derived from a second time-segment that follows at least part of the first time-segment;
determining when the plurality of first current values are within a first target range associated with the first time-segment, wherein the first target range is associated with a low analyte concentration and a second target range is associated with the second time-segment and an analyte concentration higher than the low analyte concentration of the first time-segment; and
calculating a final concentration of the analyte based on data associated with the plurality of first current values and the first set of calibration data when the plurality of first current values are within the first target range.

2. The method of claim 1, wherein calculating the final concentration of the analyte includes inputting the plurality of first current values into at least one of an iterative algorithm, an interpolative algorithm, a line-plot, and an extrapolative algorithm.

3. The method of claim 1, wherein the first set of calibration data includes at least one of a plurality of calibration curves, a lookup table, a data array, and a mathematical equation.

4. The method of claim 1, wherein the first time-segment is less than about two to about ten seconds and the second time-segment is more than about two to about ten seconds.

5. The method of claim 4, wherein the first time-segment is less than about four seconds and the second time-segment is more than about four seconds.

6. The method of claim 1, wherein at least part of the calibration data is determined using at least one of empirical data and predicted data.

7. The method of claim 1, wherein the first and second sets of calibration data are associated with different levels of hematocrit.

8. The method of claim 7, wherein the different levels of hematocrit include at least one of a high level, an intermediate level, and a low level.

9. The method of claim 1, further comprising:
measuring a plurality of second current values during the second time-segment;
determining when the plurality of second current values are within the second target range; and
calculating a final concentration of the analyte based on data associated with the plurality of second current values and the second set of calibration data when the plurality of second measured current values are within the second target range.

10. The method of claim 9, further comprising:
measuring a plurality of third current values during a third time-segment following at least part of the second time-segment; and
calculating a final concentration of the analyte based on data associated with the plurality of third current values and a third set of calibration data derived from the third time-segment, wherein a third target range is associated with an analyte concentration higher than the analyte concentration associated with the second target range.

11. The method of claim 10, wherein calculating the final concentration of the analyte includes using data associated with a predicted current value at a future time-point greater than the third time-segment.

12. The method of claim 11, wherein the predicted current value is determined using an extrapolated current decay curve based on at least one of the plurality of first current values, the plurality of second current values, and the plurality of third current values.

13. The method of claim 9, wherein calculating the final concentration of the analyte includes using data associated with a predicted current value at a future time-point greater than the second time-segment.

14. The method of claim 13, wherein the predicted current value is determined using an extrapolated current decay curve based on at least one of the plurality of first current values and the plurality of second current values.

15. The method of claim 1, wherein the first and second sets of calibration data are associated with different temperatures.

16. The method of claim 1, wherein the first time-segment is about four seconds in duration and the second time-segment is about three seconds in duration.

17. A non-transitory computer readable media, wherein the media comprises a plurality of instructions configured to direct a processor to:
measure a plurality of first current values during a first time-segment following application of a potential excitation, wherein the potential excitation is applied to a fluid sample containing an analyte, a first set of calibration data is derived from the first time-segment, and a second set of calibration data is derived from a second time-segment that follows at least part of the first time-segment;

determine when the plurality of first current values are within a first target range associated with the first time-segment, wherein the first target range is associated with a low analyte concentration and a second target range is associated with the second time-segment and an analyte concentration higher than the low analyte concentration of the first time-segment; and calculate a final concentration of the analyte based on data associated with the plurality of first current values and the first set of calibration data when the plurality of first current values are within the first target range.

18. The computer readable media of claim 17, wherein the processor is further configured to:

measure a plurality of second current values during the second time-segment;

determine when the plurality of second current values are within the second target range; and calculate a final concentration of the analyte based on data associated with the plurality of second current values and the second set of calibration data when the plurality of second measured current values are within the second target range.

19. The computer readable media of claim 18, wherein the processor is further configured to:

measure a plurality of third current values during a third time-segment following at least part of the second time-segment; and calculate a final concentration of the analyte based on data associated with the plurality of third current values and a third set of calibration data derived from the third time-segment, wherein a third target range is associated with an analyte concentration higher than the analyte concentration associated with the second target range.

20. The computer readable media of claim 19, wherein the first, second, and third sets of calibration data are associated with different temperatures.

21. The computer readable media of claim 19, wherein the first time-segment is about four seconds in duration, the second time-segment is about three seconds in duration, and the third time-segment is about three seconds in duration.

22. The computer readable media of claim 19, wherein calculating the final concentration of the analyte includes using data associated with a predicted current value at a future time-point greater than the third time-segment.

23. The computer readable media of claim 22, wherein the predicted current value is determined using an extrapolated current decay curve based on at least one of the plurality of first current values, the plurality of second current values, and the plurality of third current values.

* * * * *